(12) United States Patent
Lee et al.

(10) Patent No.: US 6,370,757 B2
(45) Date of Patent: Apr. 16, 2002

(54) METHOD FOR LOADING SHAPE MEMORY POLYMER GRIPPER MECHANISMS

(75) Inventors: Abraham P. Lee, Walnut Creek; William J. Benett, Livermore; Daniel L. Schumann, Concord; Peter A. Krulevitch, Pleasanton; Joseph P. Fitch, Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/568,615

(22) Filed: May 10, 2000

Related U.S. Application Data

(62) Division of application No. 08/984,624, filed on Dec. 3, 1997, now Pat. No. 6,240,630.

(51) Int. Cl.⁷ .......................... B23P 11/02; B21D 39/00
(52) U.S. Cl. .......................................... 29/447; 29/517
(58) Field of Search ................................ 29/421.1, 557, 29/447, 469.5, 517, 523; 606/209, 206, 207, 205; 411/909; 439/161, 932

(56) References Cited

U.S. PATENT DOCUMENTS

| | | | | |
|---|---|---|---|---|
| 3,513,429 A | * | 5/1970 | Helsop | 337/382 |
| 3,758,916 A | * | 9/1973 | Wetmore | 264/345 |
| 3,768,146 A | * | 10/1973 | Braun et al. | 29/517 |
| 4,195,902 A | * | 4/1980 | Caveney et al. | 339/258 S |
| 4,487,465 A | * | 12/1984 | Cherian | 339/30 |
| 4,720,270 A | * | 1/1988 | Guenin et al. | 439/161 |
| 4,950,258 A | * | 8/1990 | Kawai et al. | 264/230 |
| 5,037,178 A | * | 8/1991 | Stoy et al. | 385/53 |
| 5,066,091 A | * | 11/1991 | Stoy et al. | 385/98 |
| 5,630,671 A | * | 5/1997 | Larson | 403/28 |
| 5,716,410 A | * | 2/1998 | Wang et al. | 606/27 |
| 5,904,703 A | * | 5/1999 | Gibson | 606/213 |
| 5,911,737 A | * | 6/1999 | Lee et al. | 606/209 |
| 6,024,764 A | * | 2/2000 | Schroeppel | 623/1 |
| 6,059,815 A | * | 5/2000 | Lee et al. | 606/209 |
| 6,102,917 A | * | 8/2000 | Maitland et al. | 606/108 |

FOREIGN PATENT DOCUMENTS

| | | | |
|---|---|---|---|
| JP | 02049628 A | * | 2/1990 |
| JP | 2000343871 A | * | 12/2000 |

* cited by examiner

*Primary Examiner*—S. Thomas Hughes
*Assistant Examiner*—Marc Jimenez
(74) *Attorney, Agent, or Firm*—L. E. Carnahan; Alan H. Thompson

(57) ABSTRACT

A method and apparatus for loading deposit material, such as an embolic coil, into a shape memory polymer (SMP) gripping/release mechanism. The apparatus enables the application of uniform pressure to secure a grip by the SMP mechanism on the deposit material via differential pressure between, for example, vacuum within the SMP mechanism and hydrostatic water pressure on the exterior of the SMP mechanism. The SMP tubing material of the mechanism is heated to above the glass transformation temperature (Tg) while reshaping, and subsequently cooled to below Tg to freeze the shape. The heating and/or cooling may, for example, be provided by the same water applied for pressurization or the heating can be applied by optical fibers packaged to the SMP mechanism for directing a laser beam, for example, thereunto. At a point of use, the deposit material is released from the SMP mechanism by reheating the SMP material to above the temperature Tg whereby it returns to its initial shape. The reheating of the SMP material may be carried out by injecting heated fluid (water) through an associated catheter or by optical fibers and an associated beam of laser light, for example.

21 Claims, 5 Drawing Sheets

METHOD FOR LOADING SHAPE MEMORY POLYMER GRIPPER MECHANISMS

This is a divisional of application Ser. No. 08/984,624, filed Dec. 3, 1997, now U.S. Pat. No. 6,240,630.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the microgrippers, particularly to shape memory polymer gripper/release mechanisms, and more particularly to a method and apparatus for loading shape memory gripper mechanisms.

In recent years, substantial research and development has been directed to microactuators, microgrippers, etc. particularly for medical applications and capable of operating in 250–500 µm diameter applications, such as the blood vessels in the human body. Recently a shape memory polymer (SMP) material has been developed wherein above a certain temperature (Tc) the material becomes soft and can be shaped by applying pressure, and cooling to a temperature below Tc, and upon reheating the material to a temperature above Tc the material returns to its original shape.

By the use of the SMP material, microgrippers have been developed for applications such as depositing material (i.e., embolic coils) in the blood vessels. Due to the capability of the SMP materials, a small SMP tube attached to a guide wire or catheter is heated, an embolic coil, for example, is inserted in the tube, and pressure is applied to the SMP material causing it to conform about the coil, whereafter the SMP material is cooled thereby freezing the SMP material in the formed shape thereby gripping the coil, and upon reheating the SMP material the material returns to its original shape thereby releasing the coil. Such SMP microgrippers are described and claimed in copending U.S. application Ser. No. 08/807,412 filed Feb. 28, 1997, entitled, "Microfabricated Therapeutic Actuators", and assigned to the same assignee, now U.S. Pat. No. 5,911,737 issued Jun. 15, 1999.

The present invention involved the loading of the SMP tubing with deposit material for medical applications, such as an embolic coil, medication, etc., and for non-medical applications requiring the delivery and release of components in normally inaccessible areas. The apparatus of the present invention operates via differential pressure between vacuum and hydrostatic water pressure whereby an application of uniform pressure on the exterior of the SMP tubing, with a vacuum on the interior thereof causes heated SMP tubing to change shape and grip a device located therein, after which the SMP tubing is cooled and thereby freezes in its changed shape. The heating and the cooling of the SMP tubing can be accomplished by the water utilized to produce the pressure for changing the shape of the SMP tubing. The heating of the SMP tubing may also be accomplished using optical fibers and laser light. Also, either heated water passing through a catheter to which the SMP tubing is attached or laser light via optical fibers packed to the SMP tubing may be utilized to reheat the tubing and release the device therefrom.

SUMMARY OF THE INVENTION

It is an object of the present invention to enable loading of shape memory polymer material with a deposit material.

A further object of the invention is to provide a method for loading a shape memory polymer tubing with a device to be gripped and released thereby.

A further object of the invention is to provide a loading mechanism for shape memory polymer gripper/release mechanisms.

Another object of the invention is to enable loading of a shape memory polymer gripper/release mechanism utilizing differential pressure on the external and internal areas of the shape memory polymer material.

Another object of the invention is to provide loading of a shape memory polymer tube with a device to be gripped/released thereby, utilizing differential pressure between vacuum and hydrostatic water pressure.

Another object of the invention is to provide loading of a shape memory polymer gripper/release tubing utilizing pressured water which is heated and cooled on the external area of the tubing while drawing a vacuum in the internal area thereof, and applying a mechanism to areas of the heated external area of the tubing to form depressions therein which are frozen in the tubing by cooling of the external area.

Another object of the invention is to provide loading for a shape memory polymer gripper/release tubing utilizing laser heating of the tubing and differential pressure and cooling for forming depressions in the tubing for gripping a device positioned therein.

Other objects and advantages will become apparent from the following description and accompanying drawing. The invention involves the loading of a shape memory polymer SMP gripper/release mechanism with a device to be gripped and released. The invention is carried out by inserting in an SMP tubing a device to be gripped/released, utilizing differential pressure between the internal and external areas of a SMP tubing after and/or during the heating of the tube whereby depressions are formed in the tubing, and thereafter cooled the tubing causing a freezing of the thus formed depressions in the tubing which causes gripping of the device located in the tubing. Release of the device from the SMP tubing is accomplished by reheating the tubing such that it returns to its original shape. The method and apparatus of this invention requires the use of an SMP tubing having a glass transformation temperature (Tg) which when heated above Tg can be reshaped, and subsequent cooling below Tg freezes to tubing in its reshaped configuration. The heating and/or cooling can be provided by the same water applied for pressurization, or the heating can be provided by optical fibers packaged with the SMP tubing via which laser light, for example, is directed onto the tubing. The heating and cooling may be carried out during pressurization of the tubing by controlling the temperature of the water used in the differential pressure application to the tubing.

BRIEF DESCRIPTION OF THE DRAWINGS

The drawings, which form a part of the disclosure, illustrate the method and apparatus of the invention, and together with the description, exemplify and teach the principles of the invention.

DETAILED DESCRIPTION OF THE INVENTION

Figure 1:
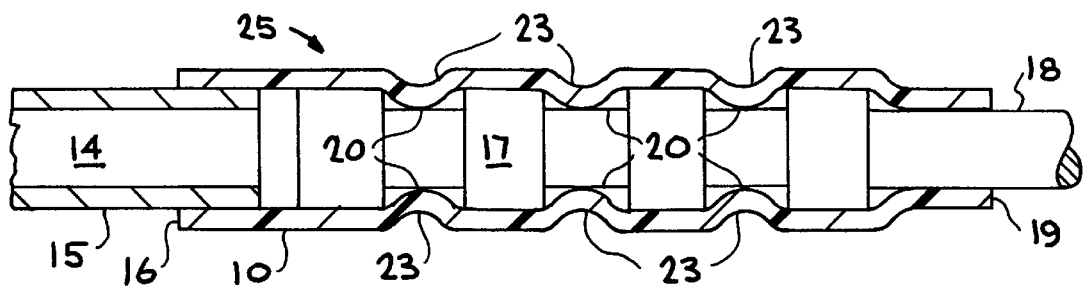
FIG. 1 is a partial cross-sectional view of an embodiment of a loaded shape memory polymer gripper/release mechanism which has been loaded in accordance with the present invention.
Figure 2:
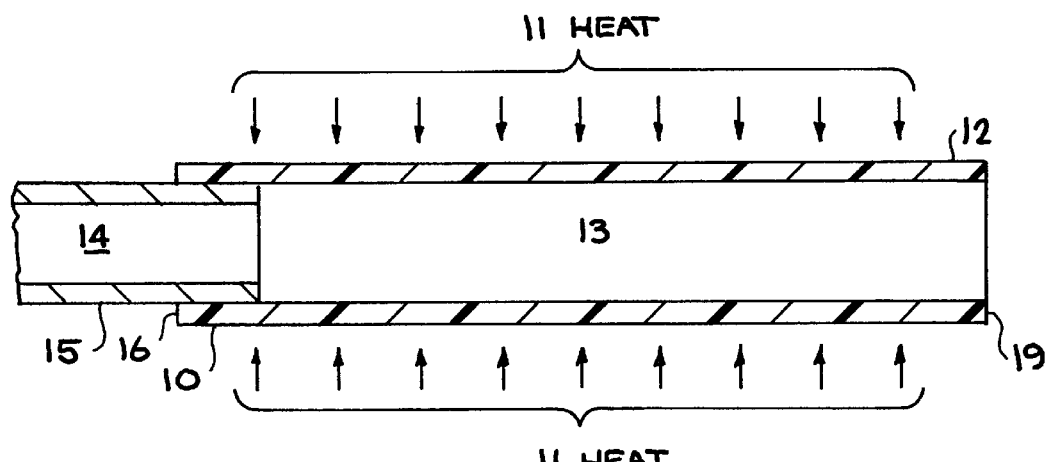
FIGS. 2–5 illustrate the method for loading the gripper/release mechanism of FIG. 1.

The present invention is directed to loading shape memory polymer gripper/release mechanisms with a deposit material. The invention involves a method and loading apparatus to enable gripping and release of a deposit material utilizing a shape memory polymer (SMP) tubing and heating the tubing to be above the glass transformation temperature (Tg) while reshaping the tubing via differential pressure, and subsequently cooling the tube to below the Tg to freeze the shape. Upon reheating the SMP tubing to a temperature above the Tg it returns to its original shape. Thus, by utilizing the SMP tubing as a gripper/release mechanism, it can be utilized for gripping/releasing devices such as embolic coils, medicine, etc. at a point of use as described and claimed in above-referenced application Ser. No. 08/807,412. The loading of the SMP gripper/release mechanism is carried in accordance with the present invention by utilizing a differential pressure between the interior and exterior of the heated SMP tubing. For example, the differential pressure between vacuum on the interior of the tubing and hystrostatic water pressure on the exterior of the tubing is used to form indentations in the SMP tubing which function to grip a device positioned in the tubing. Also, by applying vacuum to the interior, mechanical pressure can be applied to the exterior. In addition, the water utilized to produce the hydrostatic pressure on the tubing can be heated to cause the tubing temperature to raise above the Tg temperature, and the same water can be cooled to cool the tubing to below the Tg temperature which results in a freezing of the tubing in its reformed shape. Also, controls may be utilized to enable simultaneous heating and pressurization of the water, and/or simultaneous pressurization and cooling to enable a continuous heating, pressurization, and cooling sequence. Also, instead of utilizing water to heat the SMP tubing, laser light may be directed into the interior of tubing via optical fibers. Either laser light or warm water may be used to reheat the SMP tubing above its Tg temperature to allow it to return to its original shape and to release any device previously gripped therein. The apparatus of the present invention enables the application of uniform pressure to secure a grip on a deposit material via differential pressure.

In addition to medical applications for depositing materials in blood vessels in the human body, having a 250–500 μm diameter, the SMP gripper/release mechanism can be used for various non-medical applications, such as assembly of read-write heads for disk drives and other microassembly applications.

As pointed out above, the SMP gripping principle is based on the unique property of the shape memory polymer. This polymer possesses a glass transformation temperature (Tg) above which the material enters a reversible glassy phase where it becomes soft and flexible and easy to reshape. Once reshaped and cooled below Tg, the new shape is frozen in place and the material becomes hardened to over five (5) times the elastic modules of the glassy phase. Upon reheating the material to a temperature above Tg it returns to its original shape. By way of example, the Tg of the SMP material is in the range of 25 to 75° C., and the material may be manufactured to produce a Tg anywhere in this range. In the SMP tubing utilized to experimentally verify the present invention the SMP tubing, manufactured by Mitsubishi, had a Tg of 55° C.

Figure 6:
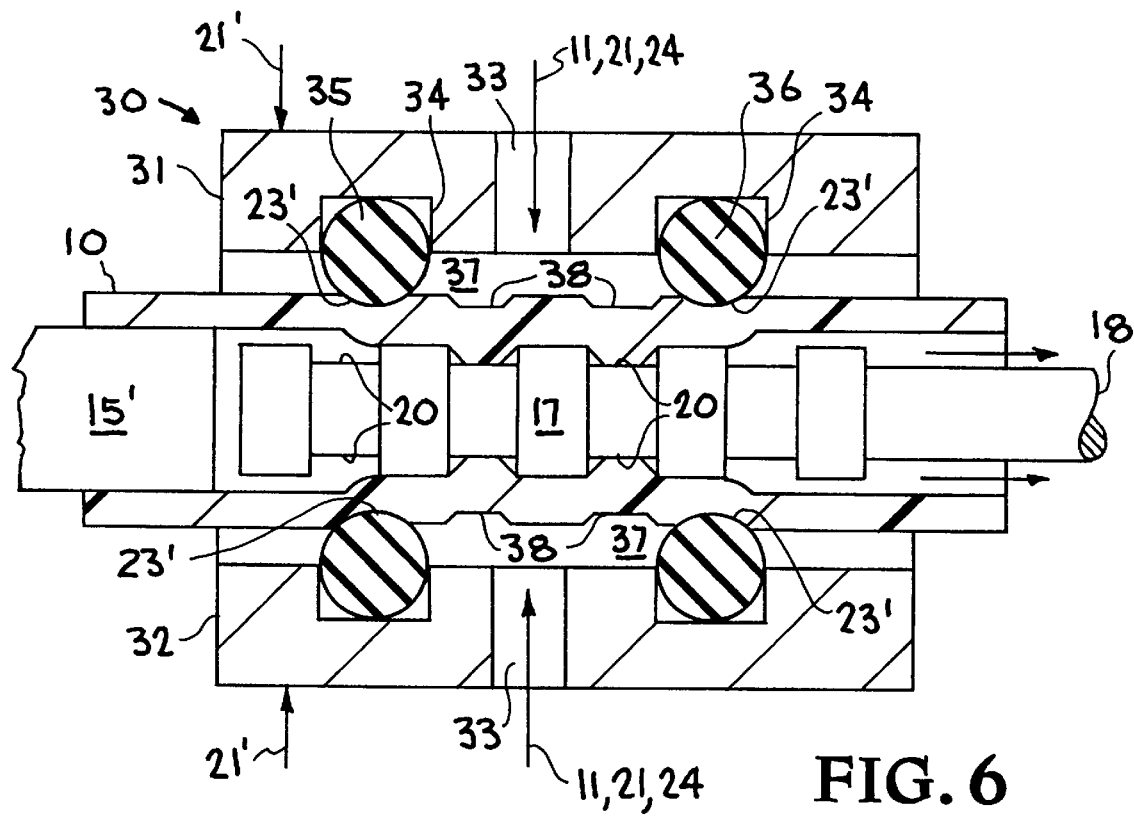
FIG. 6 illustrates schematically and in partial cross-section an embodiment of the differential pressure apparatus for loading a shape memory polymer tubing in accordance with the invention.
Figure 7:
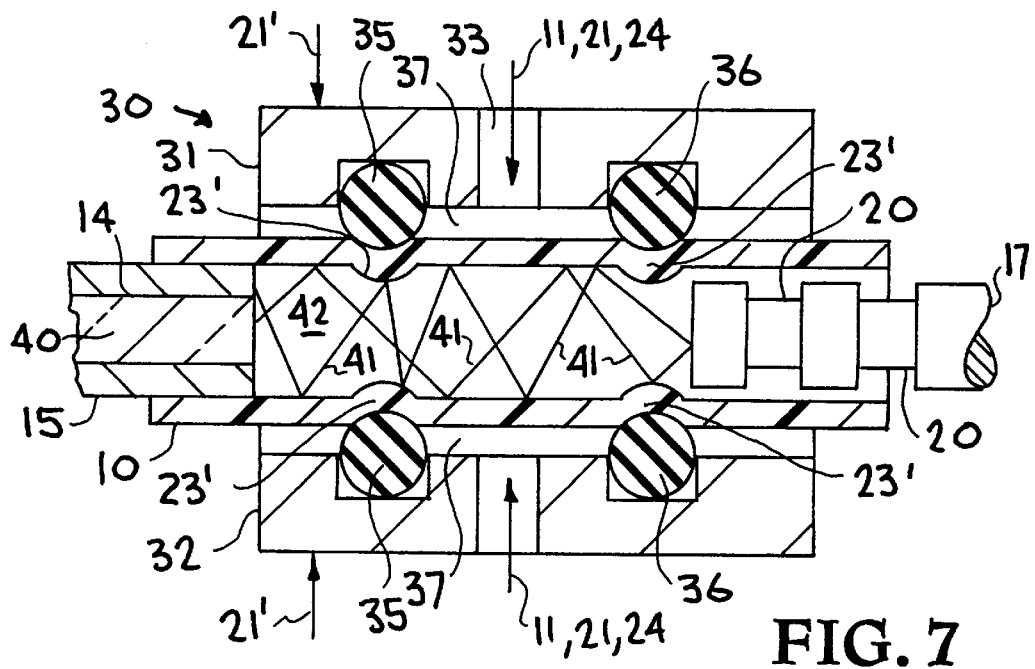
FIG. 7 illustrates schematically and in partial cross-section another embodiment of the loading apparatus, similar to FIG. 6, but utilizing laser light via optical fibers for heating the tubing, for both gripping and releasing a deposit material.
Figure 8:
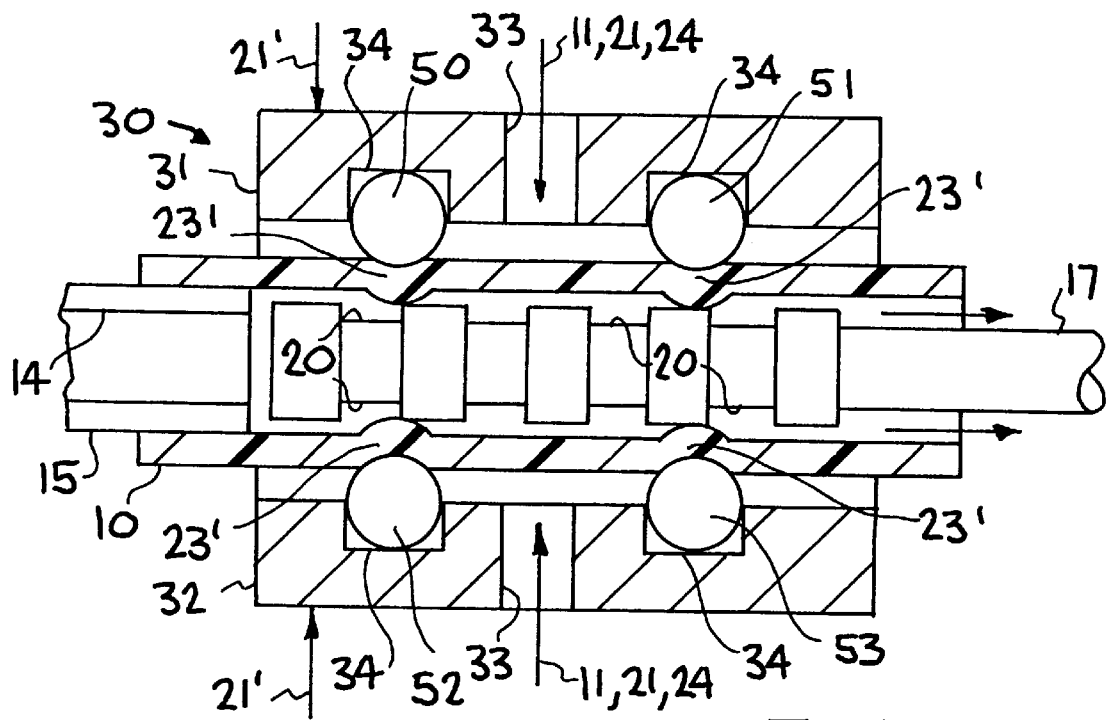
FIGS. 8–11 illustrate embodiments of loading mechanisms utilizing mechanical pressure to load a shape memory polymer tubing.
Figure 9:
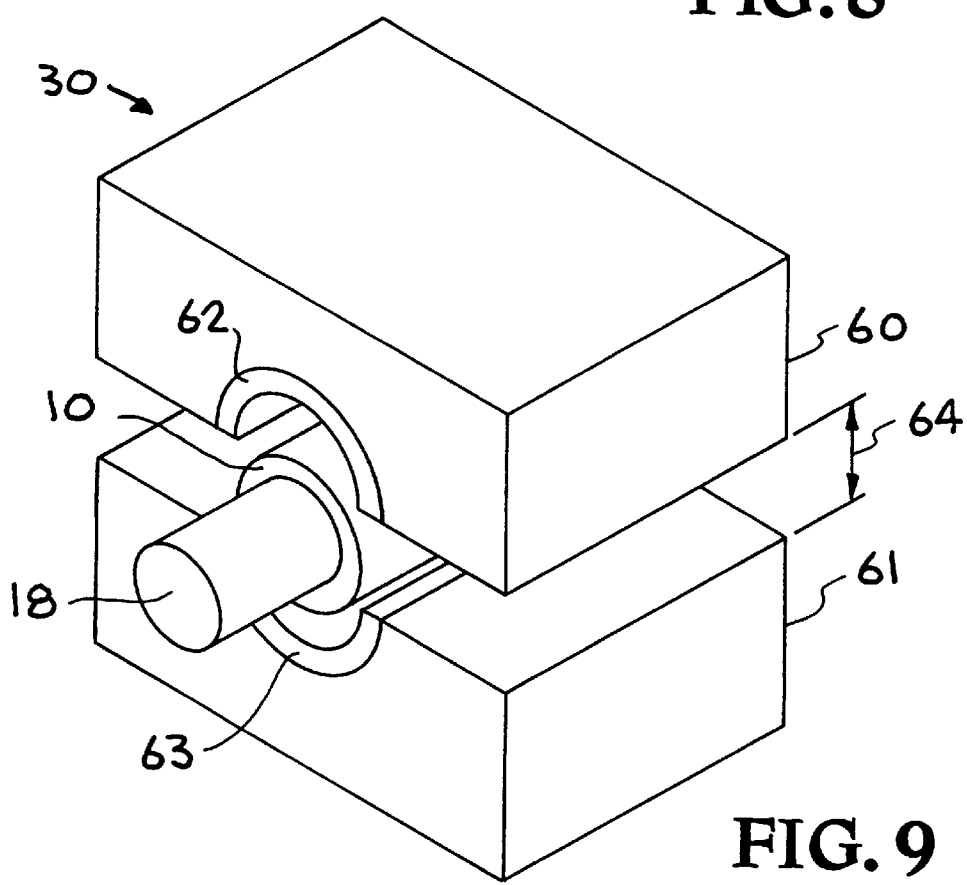
Figure 10:
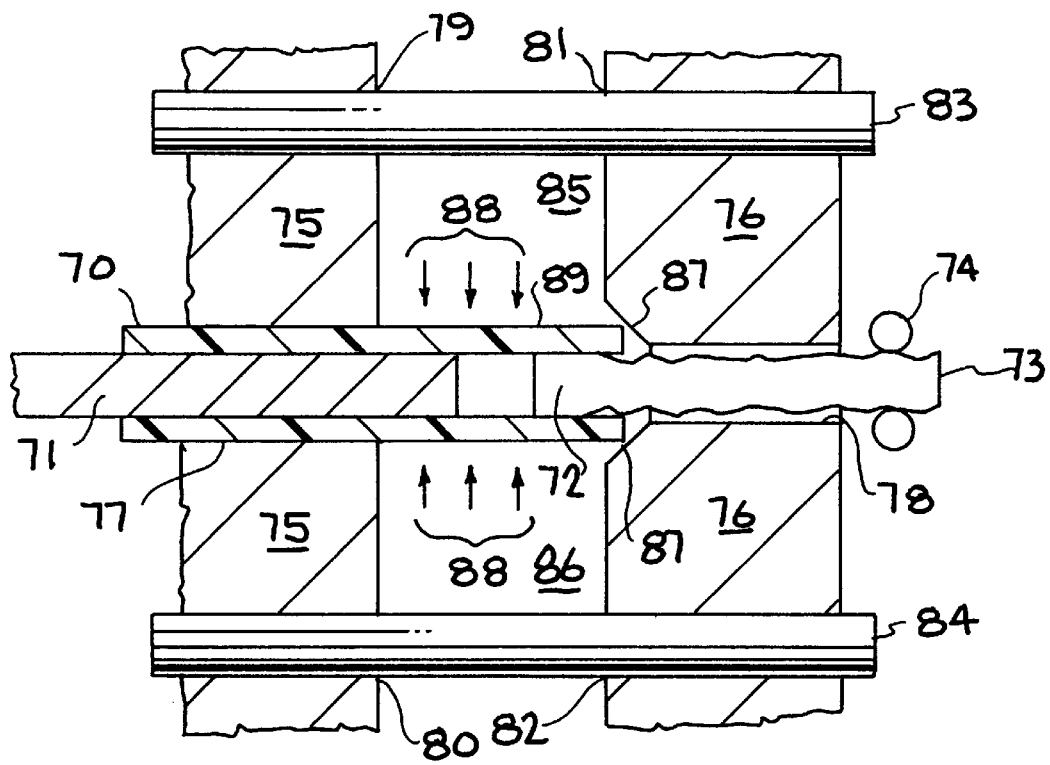

Prior to a detailed description of the method and apparatus of the present invention, a broad description thereof is as follows: First, the SMP tubing, which may be retained at the end of catheter, guide wire, or optical fiber, as illustrated in the drawings, will be heated above its transformation temperature Tg by, for example, warm water, as shown in FIG. 6, or laser light via an optical fiber, as shown in FIG. 7, and will become soft for conforming to gripped configurations, such as shown in FIGS. 1, 6, and 7. then the loading mechanism (see FIGS. 6 and 7) will provide a force to conform the SMP tubing about a deposit material or device, such as an end of an embolic coil. The loading apparatus is operated by providing a pressure difference inside and outside of the SMP tubing, for example, either by providing vacuum to the inside or hydrostatic pressure to the outside, or both. As the pressure is applied, the SMP tubing conforms into or partially into grooves in the device positioned therein and provide a packaged locking configuration. At this point, the warm water or laser light heating is replaced with cold water or other cooling means to cool the SMP tubing below the Tg to freeze it into the locking configuration. In the loading apparatus illustrated in FIGS. 6 and 7, a plurality of movable members containing O-rings are utilized to provide a sealed compartment for water to produce heating/cooling for conforming of the SMP tubing as described in detail hereinafter. These movable members may be located on opposite sides of the tubing, or spaced around tubing so that pressure thereon, such as hydrostatic water pressure moves the members into contact with the tubing and the water pressure passing through openings in the members form indentations in the tubing to secure the deposit material or device therein. In addition to the use of water to heat, pressurize and cool the SMP tube, the water can be used to heat and cool the tubing and mechanical pressure can be used to move the members against the outer surface of the SMP tube, with or without a vacuum within the tubing. Also, a combination of laser light heating and water cooling can be utilized with either hydrostatic water or mechanical pressure being applied to conform the tubing about a device therein. FIGS. 8–10 illustrate mechanical arrangements for conforming the SMP tubing about a device to be retained therein.

Referring now the FIGS. 1–5, wherein FIG. 1 illustrates an embodiment of a shape memory polymer (SMP) gripper/release mechanism, made by the method schematically illustrated in FIGS. 2–5. The method for producing the embodiment of FIG. 1, as illustrated in FIGS. 2–5 is exemplified as follows:

1. Heat is applied to an SMP tubing 10, having a glass transformation temperature of 35–65° C., as indicated by legend and arrows 11 in FIG. 2 to a temperature above Tg. The heat may be produced by a fluid such as hot water, gas, oil, etc., having a temperature of 45 to 65° C., applied to the external surface 12 of tubing 10, or by laser light transmitted to the interior surface 13 of tubing 10 via optical fibers adapted to be positioned in an opening 14 of a tube 15, secured in one end 16 of tubing 10. The optical fibers may replace the tube 15. By way of example, the tubing 10 may have an internal diameter of 200 μm to 1000 μm and an external diameter of 250 μm to 1050 μm. The tube 15 may be replaced with a solid guide wire.

Figure 3:
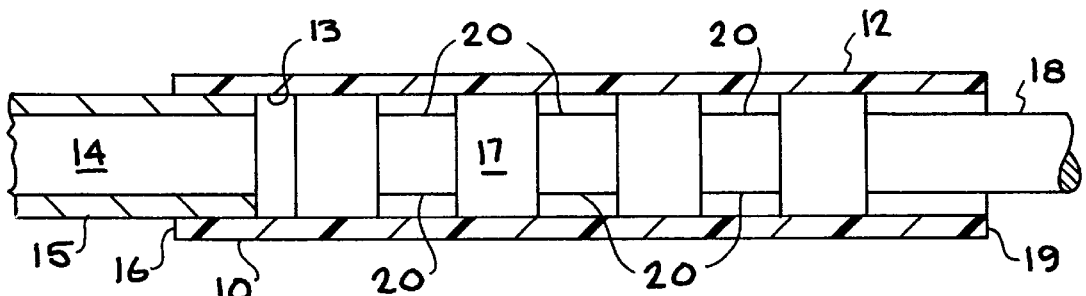

2. An end section 17 of a deposit material 18, such as an embolic coil, is inserted through an end 19 of tubing 10 into the interior of the tubing 10, as shown in FIG. 3, with end section 17 provided with one groove or a plurality of spaced grooves 20. If desired the end section 17 can be inserted prior to heating the tubing. The external diameter of end section 17 being slightly smaller than the internal diameter of tubing 10 so as to provide easy insert of the end section 17 into tubing 10. By way of example, the grooves 20 may have a width of 25 μm to 200 μm and diameter of 150 μm to about 500 μm, and spaced about a distance of 50 μm to 150 μm, with end section 17 having an external diameter of 180 μm to about 500 μm.

Figure 4:
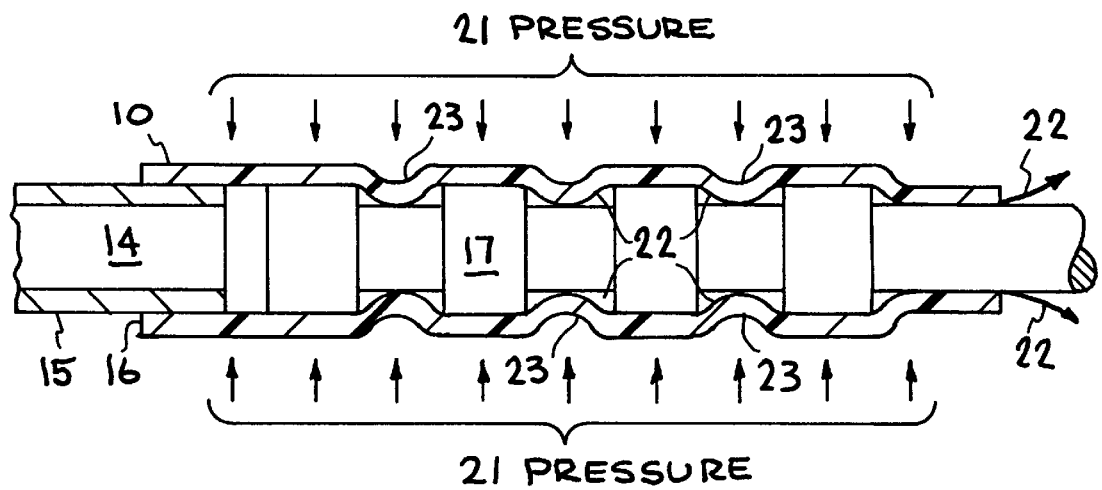

3. Pressure is applied to the external surface of heated tubing 10 as indicated by legend and arrows 21 in FIG. 4, while a vacuum is drawn on the internal surface 13 of tubing 10 as indicated by legend and arrows 22. The pressure 21 may be produced by hydrostatic water, gas, or oil pressure or mechanical pressure. The vacuum 22, produced by a pump, not shown, may be at a Torr of $10^{-4}$ to 1. If produced by hydrostatic pressure, the water used to heat the tubing 10 may be pressurized to a pressure of 800 to 3000 Torr. As seen in FIG. 4, the pressure on heated tubing 10 causes sections of the tubing adjacent grooves 20 of end section 17 to conform or indent as indicated at 23. While not shown in FIG. 4, heat 11 may be applied to tubing 10 simultaneously with pressure 21 to maintain the tubing 10 soft and pliable. Also, pressure 21 may be applied without vacuum 22 but such decreases the differential between the external and internal surfaces of tubing 10 and thus the external pressure would need to be increased to produce the same results. The indentations 23 provide a locking between tubing 10 and end section 17.

Figure 5:
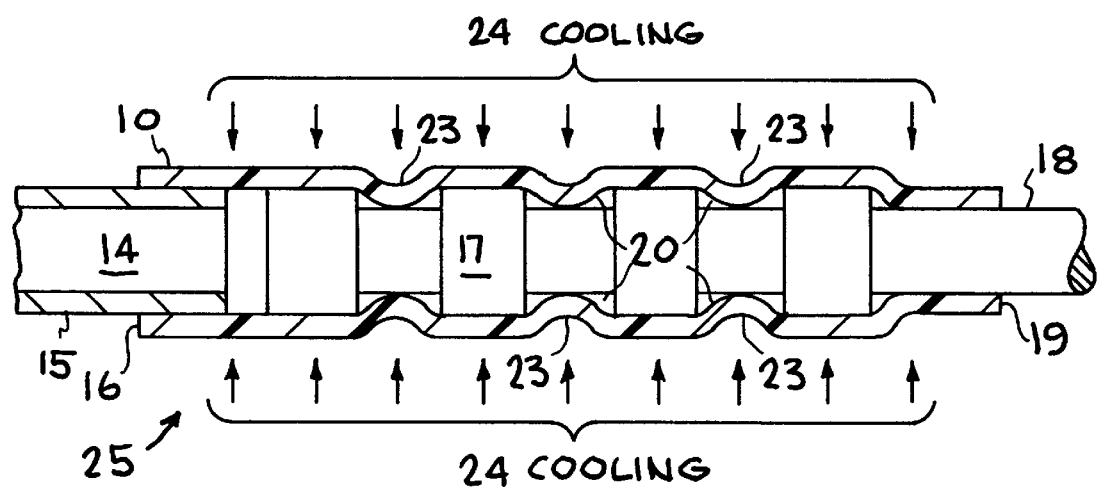

4. The tubing 10 is cooled as indicated by legend and arrows 24, as shown in FIG. 5, to a temperature below Tg, whereby the indentations 23 are frozen, and the indentations 23 of tubing 10 remain in their locked position within grooves 20 of end section 17. The cooling 24 may be carried out using cold water or other cooling means (gas, oil, etc.), and can be carried simultaneously with pressure 21 remaining applied. If cooling 24 is carried out by water, a water temperature of 5 to 25° C. may be used, and the cooling water may be the same as used for heating tubing 10 and/or for producing the hystrostatic pressure 21. Upon cooling of the tubing 10, an SMP gripper/release mechanism 25, as illustrated in FIG. 1, is produced, wherein end section 17 of the deposit material 18 is gripped by tubing 10 which is attached to tubing 15, which may, for example, be attached to a catheter or guide wire for insertion into a blood vessel of a human body, or a guide wire may be utilized in place of tubing 15 to insert the gripper release mechanism 25 and a deposit material 18 into a non-medical inaccessible area.

Upon the SMP gripper/release mechanism and loaded deposit material be positioned by the guide wire at a point of use, the SMP tubing 10 is heated to a temperature above the Tg of tubing 10, which allows the tubing 10 to revert to its original configuration thereby removing the indentations 23 in tubing 10 allowing the end section 17 of deposit material 18 to be released up removing the tubing 10 from the area of use of the deposit material 18. Reheating of the tubing 10 to above temperature Tg can be carried out, for example, by injecting hot water through the opening 14 of tubing 15 into the interior of tubing 10, or by directing laser light via optical fibers in opening 14 of tubing 15 into the interior of tubing 10. Also, a solid guide wire with optical fibers wrapped therearound may be utilized in place of tubing 15.

FIG. 6 illustrates schematically an embodiment of a loading mechanism utilizing differential pressure involving hydrostatic pressure and vacuum on the exterior and interior of the SMP tubing. Components corresponding to components of the FIG. 1 embodiment will be given corresponding reference numerals. As shown, an end section 17 of a deposit material 18 is positioned in an SMP tubing 10 secured at one end to a guide wire or optical fiber 15', the end section 17 including a plurality of spaced grooves 20. In this embodiment arrows 11/21/24 are utilized to indicate heating of, pressure on, and cooling of the SMP tubing 10, as in the operational sequence described above with respect to FIGS. 2 and 5, using water to apply the pressure (21) and warm water for heating (11), or cold water for cooling (24). A pressure differential loading mechanism generally indicated at 30 comprises a plurality of members positioned about the SMP tubing 10, two members 31 and 32 being illustrated in this embodiment, with members 31, 32 being provided with openings 33 to allow passage of heating/pressure/cooling water as indicated by arrows 11/21/24. Each of members 31–32 is provided with at least one groove 34 in which flexible members or O-rings 35 and 36 are retained around SMP tubing 10. As differential pressure indicated by arrows 21' is applied against the members 31–32 and a vacuum 22 is drawn on the interior of tubing 10, the flexible members or O-rings 35 and 36 are pressed against the external surface of heated SMP tubing 10 producing indentations 23' in the tubing, and forming a seal around the tubing 10 which defines a compartment or area 37 between O-rings 35–36 and between tubing 10 and members 31–32. As pressurized fluid (water) flows through opening 33, indentations 38 are formed in tubing 10 which provide locking between the SMP tubing 10 and the end section 17 of the deposit material 18. As described above, the pressure 21' on members 31–32 can be maintained during cooling. Note that the sealing indentations 23' in FIG. 6 have been illustrated as not extending into the grooves 20 of end section 17 while indentations 38 extend into grooves 20. The location of the indentations 23' and 38 with respect to the grooves 20 of end section 17 is dependent on the location of end section 17 within SMP tubing 10 and the location of the flexible members or O-rings 35–36.

Various modification of the loading apparatus 30 may be utilized. For example, the members 31 and 32 may be provided with a plurality of openings therein to provide for passage of heating/cooling water. Also, there may be a plurality of loading members located in spaced relation around the SMP tubing so that the sealing indentations 23' extends around the tubing. The spacing of the loading members must be such as to allow movement thereof by hydrostatic pressure, for example, or by mechanical pressure if desired, to produce the desired sealing indentations in the SMP tubing. In addition, if desired, additional flexible members or O-rings, such as shown at 35 and 36 located in additional grooves in members 31–32 may be utilized to form additional compartments or areas therebetween. Also, instead of flexible members or O-rings, balls secured in the grooves of the members 31–32 may be utilized to mechanically provide tubing indentations as shown in FIG. 8. Also, forming protruding sections on the members 31–32 in place of the grooves and flexible members or O-rings may be utilized to produce the desired indentations in the heated SMP tubing.

FIG. 7 illustrates a loading mechanism similar to that of FIG. 6 except that heating of the SMP tubing is carried out by directing laser light into the interior of the tubing via optical fibers. In FIG. 7, the end section of the deposit material is shown only partially inserted into the SMP tubing to enable clearer illustration of the laser beam heating the SMP tubing. Components similar to the components of FIG. 6 are given corresponding reference numerals. As shown, an optical fiber 40 positioned in opening 14 of tubing 15 is secured to one end of SMP tubing 10. A plurality of optical fibers 40 may be utilized. Laser light indicated at 41 is passed through optical fiber 40 into the interior 42 of SMP tubing 10 for heating the tubing to a temperature above the Tg, as described above. In this embodiment, as in FIG. 6, the end section 17 of the deposit material may be inserted into the SMP tubing after or prior to heating of the tubing. However, where laser light is utilized to heat the tubing it is more efficient to only partially insert the end section prior to heating, as shown in FIG. 7, whereby the laser light will bounce off the end of the end section 17 rather than passing out the end of the SMP tubing, thereby providing more efficient heating. By way of example the laser light 41 may be at a wavelength of 400 nm to 1000 nm. As pointed out above, a solid guide wire with optical fiber wrapped around or along the external surface thereof may be utilized in place of tubing 15 with optical fiber 40 therein.

After heating of the SMP tubing 10 by laser light as shown in FIG. 7, and the end section 17 of the deposit material is inserted into the SMP tubing, as in FIG. 6, the operation of the loading mechanism 30 as described above with respect to FIG. 6 is carried out to produce and freeze the indentations 38 in SMP tubing 10, not shown in FIG. 7.

While not shown, the hydrostatic water pressure 21, as well as the heating water and/or cooling water, may utilize the same water which flow is controlled and passes through a heating means, a pressurizing pump, and a cooling means, or means for a heating/pressurization operation and/or a pressurization/cooling operation. Such controlled systems can be readily utilized using computer control known in the art. Such heating/pressurization/cooling operations can be carried out in a controlled sequence to enable efficient manufacturing of shape memory polymer gripper/release mechanisms in various sizes and for various applications.

FIG. 8 illustrates a loading apparatus generally similar to FIG. 6 except that the indentations in the SMP tubing are formed mechanically instead of hydrostatically. Similar components to those of FIG. 6 are given corresponding reference numerals. The only structural difference from the FIG. 6 embodiment is the replacement of the flexible members or O-rings with a plurality of balls, only four (4) such balls being shown in FIG. 8 at 50–53. As in the FIG. 6 embodiment, warm or cold water indicated by arrows 11/24 is utilized to heat and/or cool the SMP tubing, but mechanical pressure indicated by arrows 21' in FIG. 8 is used to form indentations 23', the only indentations formed in SMP tubing 10. The depth of the indentations 23' is dependent on the relative location of balls 50–53 with respect to grooves 20 in end section 17 of deposit material 18. As shown in FIG. 8, the indentations 23' are sufficient to retain the end section 17 within SMP tubing 10, even though such do not fully extend into grooves 20 of end section 17 as does indentations 38 in the FIG. 6 embodiment. The mechanical pressure 21' on members 31 and 32 may be provided by conventional press technology, for example. While only four (4) balls 50–53 are shown, grooves 34 in members 31 and 32 may contain any desired number of balls, each forming an indentation 23' in the SMP tubing 10 when pressure 21' is applied.

FIG. 9 illustrates a loading apparatus utilizing a mechanical clamp arrangement. In this embodiment of an apparatus generally indicated at 30', a coil or deposit material 18 is positioned in a SMP tubing 10, as in FIG. 6, and a pair of mechanical clamps 60 and 61 having liners or members 62 and 63, constructed of a polymer or high CTE material, which are forced against the heated SMP tubing 10 when the clamps 60 and 61 are forced toward each other causing indentations in the heated SMP tubing 10, the pressure on the clamps 60 and 61 being maintained until the SMP tubing 10 has cooled below the Tg temperature thereof, whereby the indentations are frozen in the SMP tubing until it is reheated above its Tg, and the pressure on the clamps 60–61 withdrawn. Movements of the clamps 60–61 being shown by double arrow 64. The liners members 62 and 63 may be of a variety of configurations including spaced sections, protruding sections, etc., and located to form indentations at any desired location on the deposit material or coil 18 so as to retain same within the cooled SMP tubing 10.

FIG. 10 schematically illustrates a loading mechanism using mechanical damping with alignment pins. In this arrangement an SMP tubing 70 is secured at one end to a guide wire, optical fiber or catheter 71, with an end 72 of a deposit material 73 being inserted into an opposite end of SMP tubing 70, by a retain means 74. The loading mechanism comprises a pair of annular matching spaced members, only a portion of each pair shown at 75 and 76 and having openings 77 and 78, respectively, within which the SMP tube 70 and the end 72 of deposit material 73 are inserted, with opening 78 being of a smaller diameter than opening 77. Members 75 and 76 additionally include openings 79–80 and 81–82 through which alignment pins 83 and 84 are inserted to align members 75 and 76, which are spaced from each other to define compartments or areas 85 and 86. Member 76 is provided with a tapered surface 87 adjacent opening 78.

In operation of the FIG. 10 mechanism, pressure is applied to the pairs of members which cause member 75 and tapered surface 87 of member 76 to contact the SMP tubing 70 forming a seal therebetween whereafter fluid pressure indicated by arrows 88 is directed through compartments of areas 85 and 86 causing an end 89 of the SMP tubing 70 to conform to the shape of the end 72 of deposit material 73, and upon cooling the SMP tubing 70 as described above, the end 72 of deposit material 73 is retained within the end 89 of SMP tubing 70. However, pressure applied by the tapered surface 87 may be utilized as a clamping surface to cause the end of 89 of tubing 70 in conforming to the shape of the end 72 of deposit material 73.

Figure 11:
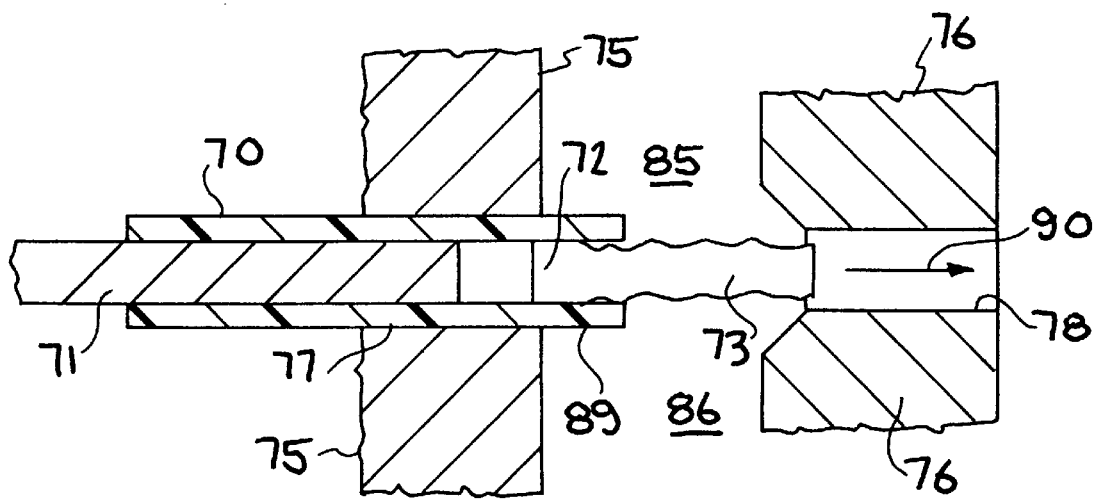

FIG. 11 illustrates an inverted version of the loading mechanism of FIG. 10, the difference being that the end 72' of deposit material 73 is inserted into the end 89 of SMP tubing 70, thus eliminating the retainer mechanism 74 of FIG. 10, whereafter the SMP tubing 70 and the deposit material 73 are inserted through opening 77 of member 75 and into opening 78 in member 76 as indicated by arrow 90 until the end 89 of SMP tubing contacts tapered surface 87 of member 76, whereafter pressure fluid is directed into areas 85 and 86 causing the end 89 of SMP tubing 70 to fully conform to the external surface of end 72 of deposit material 73, as described above. In the FIG. 11 embodiment the initial I.D. of SMP tubing 70 is slightly greater than the O.D. of the end 72 of the deposit material 73 so that the deposit material is initially retained in the end of the SMP tubing 70 by the close fit.

It has thus been shown, that the present invention provides a method and apparatus for loading shape memory polymer (SMP) gripper/release mechanism. The invention utilizes differential pressure, such as between vacuum and hydrostatic water pressure, to produce indentations in SMP tubing for retaining deposit material therein. The invention utilizes heated water or laser light to heat the SMP tubing, and water to cool the tubing after the indentations are formed to freeze same in a locking position about the deposit material. The same water may be utilized for heating, pressurization, and cooling of the SMP tubing. The invention enables the efficient and inexpensive manufacture of SMP gripper/release mechanisms for various applications, particularly those requiring operation in areas of 250–500 µm diameters.

While particular embodiments of the invention have been illustrated and/or described and particular operational sequences have been described, along with exemplary parameters, materials, etc., such are not intended to be limiting. Modifications and changes may become apparent to those skilled in the art, and it is intended that the invention be limited only by the scope of the appended claims.

The invention claimed is:

1. A method for loading a shape memory polymer to form a gripper/release mechanism retainingn a deposit material, including:

heating a quantity of shape memory polymer, having a hollow interior and having at least a section of a deposit material located in one end of the hollow interior, to a temperature above a phase transformation temperature of the shape memory polymer;

applying differential pressure across the heated shape memory polymer causing an inwardly extending change in the shape memory polymer configuration; and cooling the shape memory polymer to a temperature below the phase transformation temperature to maintain the change in the configuration of the shape memory and maintain at least contact between the interior of the shape memory polymer and at least a portion of the section of deposit material therein for retaining at least the section of deposit material in the end of the interior of the shape memory polymer.

2. The method of claim 1, additionally including heating the shape memory polymer and then removing at least the section of deposit material therefrom.

3. The method of claim 1, wherein heating the shape memory polymer is carried out, using heated fluid or laser light.

4. The method of claim 1, wherein applying a differential pressure is carried out between a vacuum and hydrostatic fluid pressure.

5. The method of claim 1, wherein cooling the shape memory polymer is carried out using cool fluid.

6. The method of claim 1, additionally including attaching the shape memory polymer to a guide wire.

7. The method of claim 1, wherein applying a differential pressure is carried out using at least mechanical pressure, and utilizing means for causing the change in shape of the shape memory polymer.

8. A method for loading a shape memory polymer to form a gripper/release mechanism retaining a deposit material, including:

heating a quantity of shape memory polymer, having at least a section of a deposit material located therein, to a temperature above a phase transformation temperature of the shape memory polymer;

applying differential pressure across the heated shape memory polymer causing an inwardly extending change in the shape memory polymer configuration; and cooling the shape memory polymer to a temperature below the phase transformation temperature to maintain the change in the configuration of the shape memory and maintain at least contact between the shape memory polymer and at least a portion of the section of deposit material therein for retaining at least the section of deposit material in the shape memory polymer, wherein the change in shape of the shape memory polymer is carried out by forming spaced seals about the shape memory polymer, and directing pressurized fluid onto the shape memory polymer intermediate the spaced seals.

9. A method for loading a gripper/release mechanism with an object, comprising:

providing a shape memory polymer, heating the shape memory polymer to a temperature above a temperature Tc, inserting an object to be loaded into one end of the shape memory polymer, applying differential pressure across the heated shape memory polymer to cause an inwardly extending change in configuration thereof for retaining the object in one end thereof, and cooling the shape memory polymer to a temperature below the temperature Tc to maintain the configuration caused by applying pressure thereto.

10. The method of claim 9, additionally including reheating the shape memory polymer to a temperature above the temperature Tc causing said shape memory polymer to return to an initial shape allowing release of an object retained therein.

11. The method of claim 9, wherein producing the differential pressure is carried out using a vacuum and a hydrostatic or mechanical pressure.

12. The method of claim 9, wherein the shape memory polymer is of a hollow configuration, and wherein applying the differential pressure is carried out across at least a portion of a wall surface of the hollow configuration.

13. The method of claim 12, wherein applying the differential pressure is carried out using vacuum and hydrostatic water pressure.

14. The method of claim 13, wherein the vacuum is applied to an interior of the hollow configuration and the hydrostatic water pressure is applied to an exterior of the hollow configuration.

15. The method of claim 9, wherein applying differential pressure to the heated shape memory polymer is carried out using a plurality of flexible members forming spaced seals about the shape memory polymer, and additionally directing fluid pressure into the area forming at least one indentation in said shape memory polymer.

16. The method of claim 9, wherein heating the shape memory polymer is carried out using heated fluid or laser light.

17. The method of claim 9, wherein heating, applying pressure to, and cooling the shape memory polymer is carried out using a quantity of fluid.

18. The method of claim 17, wherein heating, applying pressure to, and cooling the shape memory polymer is carried out using the same fluid.

19. The method of claim 9, wherein heating the shape memory polymer is carried out using at least one optical fiber and directing laser light through the at least one optical fiber onto the shape memory polymer.

20. The method of claim 19, wherein the shape memory polymer is of a tubular configuration and wherein heating the shape memory polymer is carried out by directing the laser light onto an interior of the tubular configuration.

21. The method of claim 9, wherein cooling the shape memory polymer is carried out using a quantity of cooled water capable of cooling the heated, pressurized shape memory polymer to a temperature below the temperature Tc of the shape memory polymer.

* * * * *